United States Patent
Chen et al.

(10) Patent No.: US 8,431,369 B2
(45) Date of Patent: Apr. 30, 2013

(54) METHOD FOR PREPARATION OF POLYUNSATURATED FATTY ACID-CONTAINING PHOSPHATIDYLSERINE

(76) Inventors: Su Chen, San Antonio, TX (US); Hung Kwong, San Antonio, TX (US)

( * ) Notice: Subject to any disclaimer, the term of this patent is extended or adjusted under 35 U.S.C. 154(b) by 289 days.

(21) Appl. No.: 13/015,276

(22) Filed: Jan. 27, 2011

(65) Prior Publication Data

US 2011/0124061 A1    May 26, 2011

Related U.S. Application Data

(63) Continuation-in-part of application No. 12/032,164, filed on Feb. 15, 2008, now abandoned, which is a continuation of application No. 10/762,657, filed on Jan. 21, 2004, now abandoned.

(51) Int. Cl.
*C12P 7/64* (2006.01)

(52) U.S. Cl.
USPC .................. 435/134; 435/253.5; 435/198

(58) Field of Classification Search .................. 435/134, 435/253.5, 198
See application file for complete search history.

(56) References Cited

PUBLICATIONS

Chen et al. J. Agric. Food Chem. (1996) 44: 3120-3125.*
Hosokawa et al. J. Agric. Food Chem. (2000) 48: 4550-4554.*
Chen et al. J. Chromatography B (1995) 666: 178-182.*

* cited by examiner

*Primary Examiner* — Susan Hanley
(74) *Attorney, Agent, or Firm* — Michael A. Blake

(57) ABSTRACT

A method for the preparation of the polyunsaturated fatty acids-containing phosphatidylserine, the method comprising: combining L-serine with a fish liver phosphatidylcholine having a polyunsaturated fatty acid to form a mixture; reacting the mixture with phospholipase D to effect transphosphatidylation of L-serine and the phosphatidylcholine having polyunsaturated fatty acids to produce the polyunsaturated fatty acids-containing phosphatidylserine.

1 Claim, No Drawings

METHOD FOR PREPARATION OF POLYUNSATURATED FATTY ACID-CONTAINING PHOSPHATIDYLSERINE

CROSS-REFERENCES

This application is a continuation-in-part application of U.S. Ser. No. 12/032,164, filed Feb. 15, 2008, to Su Chen and Hung Kwong, entitled "Method for Preparation of Polyunsaturated Fatty Acid-containing Phosphatidylserine", now abandoned, which is a continuation application of U.S. Ser. No. 10/762,657, filed Jan. 21, 2004, to Su Chen, entitled "Preparation of Highly Polyunsaturated Fatty Acid-Containing Phosphatidylserine and Phosphatic Acid", now abandoned, the contents of each referenced application are incorporated by reference herein in their entirety.

FIELD OF THE INVENTION

The present invention relates to the preparation of highly polyunsaturated fatty acid-containing phosphatidylserine and phosphatidic acid.

BACKGROUND OF THE INVENTION

Phosphatidylserine and phosphatidic acid are two naturally occurring phospholipid classes. Biochemical and biophysical functions of the phospholipids are well documented and appear to be determined by the composition of phospholipid fatty acid chains. Fatty acid chains with more than two double bonds are generally called highly polyunsaturated fatty acids. Laboratory experiments have shown pharmacological effects of highly polyunsaturated fatty acid-containing phosphatidylserine and phosphatidic acid molecules on enhancing cholinergic neurotransmission.

Due to the difficulty of chemically synthesizing highly polyunsaturated fatty acid-containing phosphatidylserine and phosphatidic acid molecules, chemical extraction and purification of such molecules from bovine brain, particularly the highly polyunsaturated fatty acid-containing phosphatidylserine molecules, is generally practical approach to obtain them. Unfortunately, the risk of bovine spongiform encephalopathy made the use of phosphatidylserine molecules extracted from bovine brain potentially dangerous, and the development of an alternative method to prepare highly polyunsaturated fatty acid-containing phosphatidylserine and phosphatidic acid molecules is desired and lacking. In recent years, new features of phosphatidylserine molecules have been made by phospholipase D-catalyzed transphosphatidylation of egg and soybean phosphatidylcholine and have been used as brain cell nutrients as well. But highly polyunsaturated fatty acid-containing phosphatidylserine and phosphatidic acid molecules are generally lacked in final products.

Fish liver phospholipids contain more than 65% of highly unsaturated fatty acid-containing phosphatidylcholine molecules (less than 5% of phosphatidylserine+phosphatidic acid), and this natural material is considered to be safe for the preparation of highly polyunsaturated fatty acid-containing phosphatidylserine and phosphatidic acid molecules by the phospholipase D-catalyzed transphosphatidylation procedure. Natural phosphatidylcholine can also be readily separated and purified from other phospholipids using chromatographic techniques.

SUMMARY OF THE INVENTION

The present invention relates to a method for the preparation of the polyunsaturated fatty acids-containing phosphatidylserine, the method comprising: combining L-serine with a fish liver phosphatidylcholine having polyunsaturated fatty acids to form a mixture; reacting the mixture with phospholipase D to effect transphosphatidylation of L-serine and the phosphatidylcholine having polyunsaturated fatty acids to produce the polyunsaturated fatty acids-containing phosphatidylserine.

DETAILED DESCRIPTION OF THE INVENTION

The following description and figures are meant to be illustrative only and not limiting. Other embodiments of this invention will be apparent to those of ordinary skill in the art in view of this description.

The following materials are used in the transphosphatidylation procedure:

a: Phospholipase D

Phospholipase D is an enzyme and is commercially available (Sigma Chemical Company; S. Louis, Mo.). Phospholipase D can catalyze the transfer of phosphatidyl group from phosphatylcholine to various primary alcohols.

b: L-Serine

L-Serine is a common amino acid and is commercially available as well (Sigma Chemical Company; S. Louis, Mo.). The chemical structure of L-Serine is:

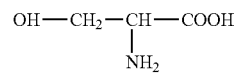

c: Fish Liver Phosphatidylcholine

Phosphatidylcholine (Lecithin) is a naturally occurring phospholipid class. Fish liver is enriched with highly polyunsaturated fatty acid-containing phosphatidylcholine molecules. The structural characterization of these molecules is mainly due to (i) a phosphocholine moiety linked to the sn-3 position of the glycerol backbone; (ii) a variety of diacyl fatty acid chains esterified to the sn-1 and sn-2 positions of the glycerol backbone, and (iii) location of double bond(s) (between 1-6) within unsaturated fatty acid chains with a number of carbon atoms (between 14-22). Fish liver phosphatidylcholine class consists of more than 10 phosphatidylcholine molecules, and a fish liver phosphatidylcholine molecule contains one of any fatty acid chains, which is esterified at sn-1 position of the glycerol backbone, and another one of any fatty acid which is esterified at sn-2 position of the glycerol backbone. The chemical characterization of fish liver phosphatidylcholine species is:

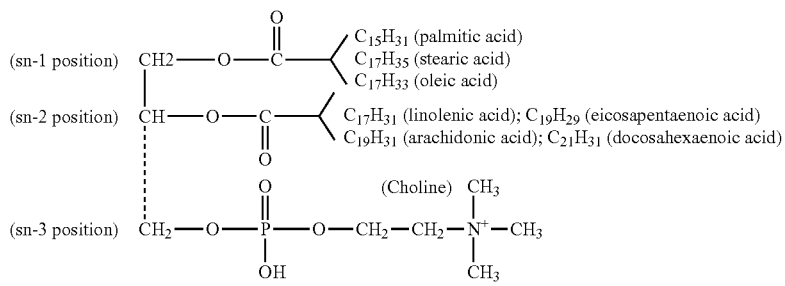

Reference: Lipid Nomenclature, Lipids, Vol. 12, 455-468 (1977))

Laboratory experiments have shown that these highly polyunsaturated fatty acid chains in phospholipid molecules are usually esterified at sn-2 position of the glycerol backbone. Of the phosphatidylcholine molecules from fish liver, the fatty acid chains esterified at the sn-1 position of the glycerol backbone are different, usually including palmitic acid ($C_{16}H_{31}O_2$; containing none of double bond); stearic acid ($C_{18}H_{35}O_2$; containing none of double bond); and oleic acid ($C_{18}H_{33}O_2$; containing one double bone). The fatty acid chains esterified at the sn-2 position of the glycerol backbone are different too, usually including linolenic acid ($C_{18}H_{31}O_2$; containing two double bonds); arachidonic acid ($C_{20}H_{31}O_2$; containing four double bonds), eicosapentaenoic acid ($C_{20}H_{29}O_2$; containing five double bonds); and docosahexaenoic acid ($C_{22}H_{31}O_2$; containing six double bonds)(See Reference: Su Chen and M. Claeys, J. Agr. Food Chem. Vol. 44, 2416-2423 (1996)).

Phospholipase D-Catalyzed Transphosphatidylation of Phosphatidylcholine (P. Comfurius and R. F. A. Zwaal, Biochim. Biophys. Acta, Vol. 488, p 36-42 (1977)).

At the presence of a L-Serine, a choline moiety within phosphatidylcholine can be replaced by a L-Serine, with phospholipase D-catalyzed transphosphatidylation of phosphatidylcholine, to form phosphatidylserine by this one-step procedure, and phosphatidic acid is also produced as a side product in final products. After the transphosphatidylation, the fatty acid chains esterified at sn-1 and sn-2 positions of the glycerol backbone within final products phosphatidylserine and phosphatidic acid molecules are almost identical to those within phosphatidylcholine precursors used.

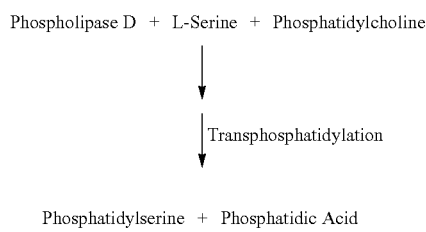

See Reference: P. Comfurius and R. F. Zwaal, Biochim. Biophys. Acta. Vol. 488, p 36-42 (1977))

Characterization of the phosphatidylserine and phosphatidic acid obtained by phospholipase D-catalyzed transphosphatidylation of fish liver phosphatidylcholine a: Chemistry After the replacement of a choline moiety at the sn-3 position of the glycerol backbone with an L-serine by phospholipase D-catalyzed transphosphatidylation of fish liver phosphatidylcholine, final products are phosphatidylserine and phosphatidic acid.

The fatty acid chains esterified at sn-1 and sn-2 positions of final products phosphatidylserine and phosphatidic acid molecules are almost identical to those within fish liver phosphatidylcholine precursors after the transphosphatidylation.

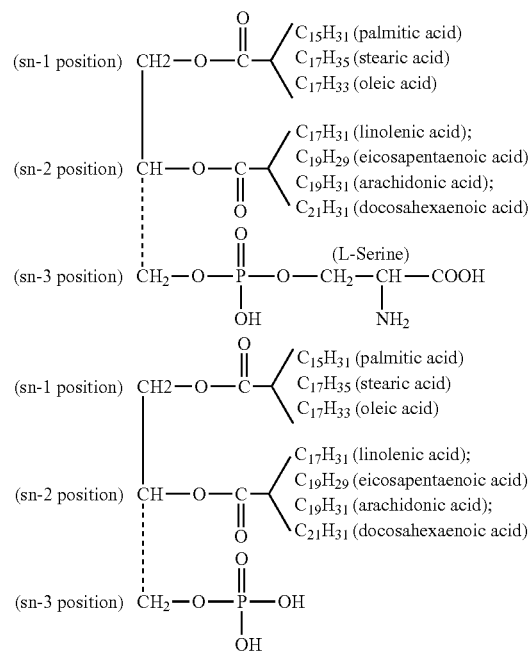

Laboratory experiments have shown that highly polyunsaturated fatty acid-containing phosphatidylserine and phosphatidic acid molecules are more effective as brain cell nutrients on enhancing cholinergic neurotransmission.

EXAMPLE 1

The Preparation of the Polyunsaturated Fatty Acids-Containing Phosphatidylserine from the Blue Fish Liver Phosphatidylcholine Tiny fragments of the frozen blue fish liver (about 500 grams) were made with an electronic blender and were then mixed with about 20 volumes of cold acetone string for about 30 min at about 4° C. After removing the liquid solution, the liver fragments, now the pellets were roughly dried under nitrogen, and then the pellets were homogenized with about 50 volumes (v/v) of ethyl acetate/ethanol (2/1; v/v) stirring for more than about 5 hours at the room temperature. After filtering and followed by evaporation of the solvent, and approximately 40 grams of the lipid extract were obtained. For the purification of the fish liver phosphatidylcholine, the lipid extract were mixed with 30 volumes (v/v) of acetone, and then the mixture was stirred at 35° C. for about 1 hour. The clear solution was kept at about −20° C. for about 8 hours, leading to the precipitation of the fish liver phospholipids. After rapid filtration and followed by dryness with nitrogen, the blue fish liver phospholipids were obtained, consisting of about 80% of the purified fish liver phosphatidylcholine, about 15% of lysophosphatidylcholine and about 5% of other lipids, monitored by thin-layer chromatography combined with phosphoric assay.

About 80 mL of acetate buffer (about 0.2M; pH 5.5), containing about 40 mM of calcium chloride and about 40 grams of L-serine, were prepared at about 45° C. and then placed in a jacketed reactor with a stirring mixer and a reflux condenser. Then about 10 grams of the fish liver phospholipid containing about 80% of the fish liver phosphatidylcholine were added into the reactor. The enzymatic reaction was started by adding about 100 Units of phospholipse D (*Streptomyces* sp) for more than about 15 hours at about 45° C. with stirring and flushing with nitrogen. Once the reaction was over, the reactor was unloaded with about 1000 mL of methyl-tert-butyl ether at about 5° C. with stirring about 5 min, leading to the formation of the two separated phases. After taking off the down phase, the phosphatidylserine and other lipids were in the up-phase, followed by the solvent washing with about 500 mL of water. After evaporation of the up-phase ether, the phospholipid mixture was redissolved in hexane. After dry under vacuum, finally approximately 9.6 grams of the final phospholipid product was obtained, consisting of about 30-35% of the transphosphatidylated fish liver phosphatidylserine, monitored by thin-layer chromatography and followed by the phosphoric assay, without any further purification.

EXAMPLE 2

The Preparation of the Polyunsaturated Fatty Acids-Containing Phosphatidylserine from the Tuna Fish Liver Phosphatidylcholine Followed by Chromatography Purification Tiny fragments of the frozen tuna fish liver (500 grams) were made with an electronic blender and were then mixed with about 20 volumes of cold acetone stirring for about 30 min at about 4° C. After removing the liquid, the liver fragments were dried under nitrogen, and then the pellets were homogenized with about 50 volumes (v/v) of ethyl acetate/ethanol (2/1; v/v) stirring more than about 5 hours at the room temperature. After filtering and followed by evaporation of the solvent, the lipid extract was obtained. For the purification of the fish liver phosphatidylcholine, the lipid extract was mixed with about 30 volumes (v/v) of acetone, and then stirring at about 35° C. for about 1 hour. After rapidly filtering, the clear solution was kept at about −20° C. for about 8 hours, leading to the precipitation of the tuna fish liver phospholipid. After a rapid filtration and followed by dryness under vacuum, the fish liver phospholipids were obtained, consisting of about 70% of the purified fish liver phosphatidylcholine, about 10% of lysophosphatidylcholine and about 20% of other lipids, analyzed by thin-layer chromatography separation and followed by the phosphoric assay About 80 mL of acetate buffer (0.2M; pH 5.5), containing about 40 mM of calcium chloride and about 40 grams of L-serine, were prepared at about 45° C. and then placed in a jacketed reactor with a stirring mixer and a reflux condenser. About 10 grams of the fish liver phospholipids having about 70% fish liver phosphatidylcholine was added into the reactor. The reaction was started by adding about 100 Units of phospholipse D (*Streptomyces* sp) for more than about 18 hours at about 45° C. with stirring and flushing with nitrogen. Once the reaction was over, the reactor was unloaded with about 1000 mL of methyl-tert-butyl ether at about 45° C. stirring about 5 min, leading to the formation of the two separated phases. After taking off the down phase, a phospholipid mixture was in the up-phase, and followed by drying.

The transphosphatidylated fish liver phosphatidylserine was further purified by the Q-Sepharose Fast Flow. The phospholipid product (about 9.7 grams) was redissolved in chloroform/methanol (60:40; v/v) and applied onto a column containing the anion-exchange resin (Q-Sepharose Fast Flow; approximately 200 mL), which was washed with (i) 2×3 bed volumes of chloroform/methanol/1 M sodium acetate (30:60:8; v/v), (ii) 2×3 bed volumes of chloroform/methanol/water (30:60:8; v/v), and (iii) 2×5 bed volumes of chloroform/methanol (60:40; v/v). The fish liver phosphatidylcholine, sphingomylie, lysophosphatidylcholine, and phosphatidylethanolamine were eluted by 3 bed volumes of chloroform/methanol (60:40; v/v), followed by 1 bed volume of chloroform/methanol (40:60; v/v). Finally, the transphosphatidylated fish liver phosphatidylserine were eluted with 3 bed volumes of acetic acid/chloroform (5:1;v/v). A by-product phosphatidic acid was remained on the resin. Acid-free powder of the phospholipid mixture including phosphatidylserine was obtained by lyophilization. The transphosphatidylated fish liver phosphatidylserine is approximately 85% by weight in the final product. Finally, the fish liver phosphatidylserine salt was precipitated by the slow addition of a 4.5 M sodium acetate solution in water in ethanol.

EXAMPLE 3

Gas Chromatographic Analyses of the Hydrolyzed Fatty Acids from the Transphosphatidylated Fish Liver Phpsphatidylserine Samples Gas chromatographic analyses of fatty acid methyl esters in the blue and tuna liver transphosphatidylated phosphatidylserine were performed with flame ionization detection. The fatty acid methyl esters derived from the two products were identified by comparing retention time values with those of known methylated fatty acid standards. The results are shown in Table 1 below.

TABLE 1

| Fatty Acid Profiles of the Transphosphatidylated Fish Liver Phosphatidylserine (T-PS) | | | | | | | | | |
|---|---|---|---|---|---|---|---|---|---|
| | [14:0] | [16:0] | [16:1] | [18:0] | [18:1] | [18:2] | [18:3] | [19:0] | [20:0] | [20:1] |
| T-PS (Blue fish) | 30[a] | 1 | 7 | 4 | — | — | — | — | — | — |
| T-PS (Tuna fish) | 20 | 1 | 13 | 4 | — | — | — | — | — | — |

| | [20:4] | [20:5] | [22:0] | [22:1] | [22:4] | [22:5] | [22:6] | [Others] | [Total %] |
|---|---|---|---|---|---|---|---|---|---|
| T-PS (Blue fish) | 9 | 4 | — | — | — | 8 | 35 | 2 | 100 |
| T-PS (Tuna fish) | 5 | 7 | — | — | — | 9 | 37 | 4 | 100 |

[a]Actual fatty acid profile obtained by GC analyses;

Data in Table 1 have shown clearly that the percentage of polyunsaturated fatty acids, in particular docosahexaenoic acid in the transphosphatidylated fish liver phosphatidylserine is higher than that in bovine cortex phosphatidylserine (http://www.fda.gov/Food/LabelingNutrition/LabelClaims/QualifiedHealthClaims/ucm073006.htm). Because the fish liver lipids have been recommended as food and dietary supplement (Bechtel and Oliveira, Chemical characterization of liver lipid and protein from cold-water fish species, Journal of Food Science, Vol. 71, S480 (2006)), the transphosphatidylated fish liver phosphatidylserine is considered to be the one of qualified alternatives of bovine cortex phosphatidylserine that was used as drug before (http://www.fda.gov/Food/LabelingNutrition/LabelClaims/QualifiedHealthClaims/ucm072993.htm).

It is worth to state here again that the collection and storage of the fish liver from the fish species, compared with collecting and storaging brain, squid skin and other small organs from marine animals as the starting material, is much easier and has the remarkable advantage over other procedures in a large scale of industrial preparation. These results establish that the fish liver by-product is the novel and available material from marine resource for a large scale industrial preparation of the transphosphatidylated fish liver phosphatidylserine.

The advantages of the present invention are the production of highly polyunsaturated fatty acid-containing phosphatidylserine and phosphatidic acid molecules, which are made by phospholipase D-catalyzed transphosphatidylation of fish live phosphatidylcholine, are much safer when they are used as brain cell nutrients, without the risk of bovine spongiform encephalopathy. Further, choosing fish liver phosphatidylcholine as a precursor to prepare highly polyunsaturated fatty acid-containing phosphatidylserine and phosphatidic acid molecules by the phospholipase D-catalyzed transphosphatidylation procedure is more economic with potentially industrial preparation, compared with small sizes of materials to be used as precursors, such as fish brain and squid skin phosphatidylcholine molecules that also contain highly polyunsaturated fatty acid chains.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for the preparation of polyunsaturated fatty acid-containing phosphatidylserine, the method comprising:
   blending about 500 grams of frozen tuna fish liver into small pieces via an electronic blender;
   mixing the about 500 grams of the resultant blended tuna fish liver with 20 volumes of cold acetone to obtain a mixture;
   stirring the mixture for about 30 min at about 4° C.;
   removing the liquid from the resultant stirred mixture to obtain liver fragments;
   drying the liver fragments under nitrogen to obtain dried liver fragments;
   homogenizing the dried liver fragments with 50 volumes (v/v) of ethyl acetate/ethanol at a ratio of 2/1 v/v and stirring for more than about 5 hours at the room temperature to obtain a homogenized mixture;
   filtering the homogenized mixture to produce a filtered mixture;
   evaporating the filtered mixture to obtain a lipid extract;
   mixing the lipid extract with about 30 volumes (v/v) of acetone to obtain an acetone mixture;
   stirring the acetone mixture at about 35° C. for about 1 hour to obtain a stirred mixture;
   rapidly filtering the stirred mixture;
   keeping the resulting clear solution at about −20° C. for about 8 hours, thereby precipitating tuna fish liver phospholipid;
   rapidly filtering and then drying under vacuum the tuna fish liver phospholipid to obtain fish liver phospholipids of about 70% purified fish liver phosphatidylcholine, about 10% of lysophosphatidylcholine and about 20% of other lipids;
   preparing about 80 mL of 0.2 M acetate buffer at a pH 5.5 containing 40 mM of calcium chloride and 40 grams of L-serine at 45° C. and then placing the resultant mixture in a jacketed reactor with a stirring mixer and a reflux condenser;
   adding about 10 grams of the fish liver phospholipids having about 70% fish liver phosphatidylcholine into the jacketed reactor;
   starting a reaction by adding 100 Units of phospholpse D from *Streptomyces* sp for more than about 18 hours at about 45° C. with stirring and flushing with nitrogen;
   allowing the reaction to complete;
   unloading the jacketed reactor with 1000 mL of methyl-tert-butyl ether at 45° C. and stirring about 5 min, leading to the formation of two separated phases;
   taking off the lower phase, wherein a phospholipid mixture is left in the upper-phase, drawing off the upper phase and drying the upper phase and dissolving the resultant phospholipid product in an amount of about 9.7 grams in chloroform/methanol at a ratio of 60:40 (v/v) and applying the resultant mixture onto a column containing about 200 mL anion-exchange resin; and washing with (i) 2×3 bed volumes of chloroform/methanol/1 M sodium acetate in a ratio of 30:60:8 (v/v), (ii) 2×3 bed volumes of chloroform/methanol/water in a ratio of 30:60:8 (v/v), and (iii) 2×5 bed volumes of chloroform/methanol in a ratio of 60:40 (v/v);
   eluting fish liver phosphatidylcholine, sphingomylie, lysophosphatidylcholine, and phosphatidylethanolamine by 3 bed volumes of chloroform/methanol in a ratio of 60:40 (v/v), followed by 1 bed volume of chloroform/methanol in a ratio of 40:60 (v/v);
   eluting a phospholipid mixture contain transphosphatidylated fish liver phosphatidylserine with 3 bed volumes of acetic acid/chloroform in a ration of 5:1 (v/v); leaving a by-product phosphatidic acid on the resin;
   lyophilizing the phospholipid mixture to obtain an acid-free powder of the phospholipid mixture wherein transphosphatidylated fish liver polyunsaturated fatty acids-containing phosphatidylserine is approximately 85% by weight; and
   precipitating the resultant liver polyunsaturated fatty acids-containing phosphatidylserine salt by the slow addition of an about 4.5 M sodium acetate solution in water in ethanol.

* * * * *